(12) United States Patent
Kuo et al.

(10) Patent No.: US 12,023,107 B2
(45) Date of Patent: Jul. 2, 2024

(54) METHOD, SYSTEM AND APPARATUS FOR MAINTAINING PATIENT REGISTRATION IN A SURGICAL NAVIGATION SYSTEM

(71) Applicant: SYNAPTIVE MEDICAL INC., Toronto (CA)

(72) Inventors: Audrey Yu-Ching Kuo, Toronto (CA); Kirusha Srimohanarajah, Toronto (CA); Gal Sela, Toronto (CA); Alexander Gyles Panther, Toronto (CA); Kelly Noel Dyer, Toronto (CA)

(73) Assignee: Synaptive Medical Inc.

( * ) Notice: Subject to any disclaimer, the term of this patent is extended or adjusted under 35 U.S.C. 154(b) by 687 days.

(21) Appl. No.: 17/301,988

(22) Filed: Apr. 21, 2021

(65) Prior Publication Data
US 2021/0259784 A1    Aug. 26, 2021

Related U.S. Application Data

(63) Continuation of application No. 15/899,753, filed on Feb. 20, 2018, now Pat. No. 10,987,173.

(30) Foreign Application Priority Data

Feb. 21, 2017  (CA) ..................... 2958624

(51) Int. Cl.
*A61B 34/20* (2016.01)
*A61B 5/00* (2006.01)
*A61B 5/055* (2006.01)
*A61B 5/11* (2006.01)
*A61B 90/00* (2016.01)
*G01R 33/28* (2006.01)

(52) U.S. Cl.
CPC ............ *A61B 34/20* (2016.02); *A61B 5/0037* (2013.01); *A61B 5/0064* (2013.01); *A61B 5/055* (2013.01); *A61B 5/1114* (2013.01); *A61B 5/706* (2013.01); *A61B 90/39* (2016.02); *G01R 33/283* (2013.01); *A61B 2034/2051* (2016.02); *A61B 2034/2065* (2016.02); *A61B 2090/363* (2016.02); *A61B 2090/364* (2016.02); *A61B 2090/3954* (2016.02)

(58) Field of Classification Search
CPC ...... A61B 34/20; A61B 5/0037; A61B 5/0064
See application file for complete search history.

*Primary Examiner* — Jason M Ip

(57) ABSTRACT

A device and methods for maintaining patient registration in surgical navigation, involving: obtaining a patient position in a tracking system frame of reference, based on a fiducial marker array affixed in a first position relative to the patient; receiving an initial surface scan depicting the patient and the fiducial array; responsive to receiving an intraoperative image depicting the patient: obtaining a position, in the tracking system frame of reference, of the fiducial array affixed in a second position relative to the patient; receiving a secondary surface scan depicting the patient and the fiducial array; detecting a deviation in a position of the fiducial marker array relative to the patient between the initial and secondary surface scans; and applying the deviation to the position of the patient to generate an updated position of the patient in the tracking system frame of reference, based on the fiducial array affixed in the second position.

20 Claims, 10 Drawing Sheets

METHOD, SYSTEM AND APPARATUS FOR MAINTAINING PATIENT REGISTRATION IN A SURGICAL NAVIGATION SYSTEM

CROSS-REFERENCE TO RELATED APPLICATION(S)

This document is a continuation application which claims the benefit of, and priority to: U.S. patent application Ser. No. 15/899,753, filed on Feb. 20, 2018, entitled "METHOD, SYSTEM AND APPARATUS FOR MAINTAINING PATIENT REGISTRATION IN A SURGICAL NAVIGATION SYSTEM," and Canadian Patent Application No. 2958624, filed on Feb. 21, 2017, entitled "METHOD, SYSTEM AND APPARATUS FOR MAINTAINING PATIENT REGISTRATION IN A SURGICAL NAVIGATION SYSTEM," all of which are incorporated herein by reference in their entirety.

FIELD

The specification generally relates to medical imaging and specifically relates to a method, system, and apparatus for maintaining patient registration in a medical imaging system.

BACKGROUND

Navigation systems are employed in various surgical contexts, permitting surgical tools to be tracked during a procedure and displayed alongside both preoperative and intraoperative patient images, surgical planning data, and the like. Such systems generally require that a patient's position be registered with a tracking system, permitting the patient to be depicted alongside tracked surgical tools, for example. Registration may be accomplished, for example, by affixing fiducial markers in a known position relative to the patient. However, the markers may need to be removed. For example, when repositioning the patient to obtain an intraoperative, e.g., magnetic resonance imaging, MRI, image of the patient, as well as when repositioning the patient for further surgical intervention after the intraoperative image is captured. Removal of the fiducial markers results in loss of patient registration, which can reduce the accuracy of intraoperative image capture, and may necessitate a time-consuming repetition of the patient registration process after the intraoperative image is captured. Additionally, positioning the patient within an imaging device such as an MRI scanner typically requires manual verification and adjustment of imaging configuration to account for the patient's orientation within the imaging device. Such verification and adjustment can be time-consuming procedures.

SUMMARY

According to an aspect of the present disclosure, a method of maintaining patient registration in a surgical navigation system, comprises: obtaining, at a computing device of the medical imaging system, a position of a patient in a tracking system frame of reference, based on a fiducial marker array affixed in a first position relative to the patient; receiving, at the computing device, an initial surface scan depicting the patient and the fiducial marker array in the first position; responsive to receiving, from a medical imaging device, an intraoperative image depicting the patient: obtaining a position, in the tracking system frame of reference, of the fiducial marker array affixed in a second position relative to the patient; receiving a secondary surface scan depicting the patient and the fiducial marker array in the second position; detecting a deviation in a position of the fiducial marker array relative to the patient between the initial and secondary surface scans; and applying the deviation to the position of the patient to generate an updated position of the patient in the tracking system frame of reference, based on the fiducial marker array affixed in the second position.

According to another aspect of the present disclosure, a computing device for maintaining patient registration in a surgical navigation system, comprising: a communications interface configured to connect with a surface scanner and a medical imaging device; a processor interconnected with the communications interface, the processor configured to: obtain a position of a patient in a tracking system frame of reference, based on a fiducial marker array affixed in a first position relative to the patient; receive an initial surface scan from the surface scanner, depicting the patient and the fiducial marker array in the first position; responsive to receiving, from the medical imaging device, an intraoperative image depicting the patient: obtain a position, in the tracking system frame of reference, of the fiducial marker array affixed in a second position relative to the patient; receive a secondary surface scan depicting the patient and the fiducial marker array in the second position; detect a deviation in a position of the fiducial marker array relative to the patient between the initial and secondary surface scans; and apply the deviation to the position of the patient to generate an updated position of the patient in the tracking system frame of reference, based on the fiducial marker array affixed in the second position.

BRIEF DESCRIPTION OF THE DRAWINGS

Embodiments are described with reference to the following figures, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps, or components are included. These terms are not to be interpreted to exclude the presence of other features, steps, or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings.

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
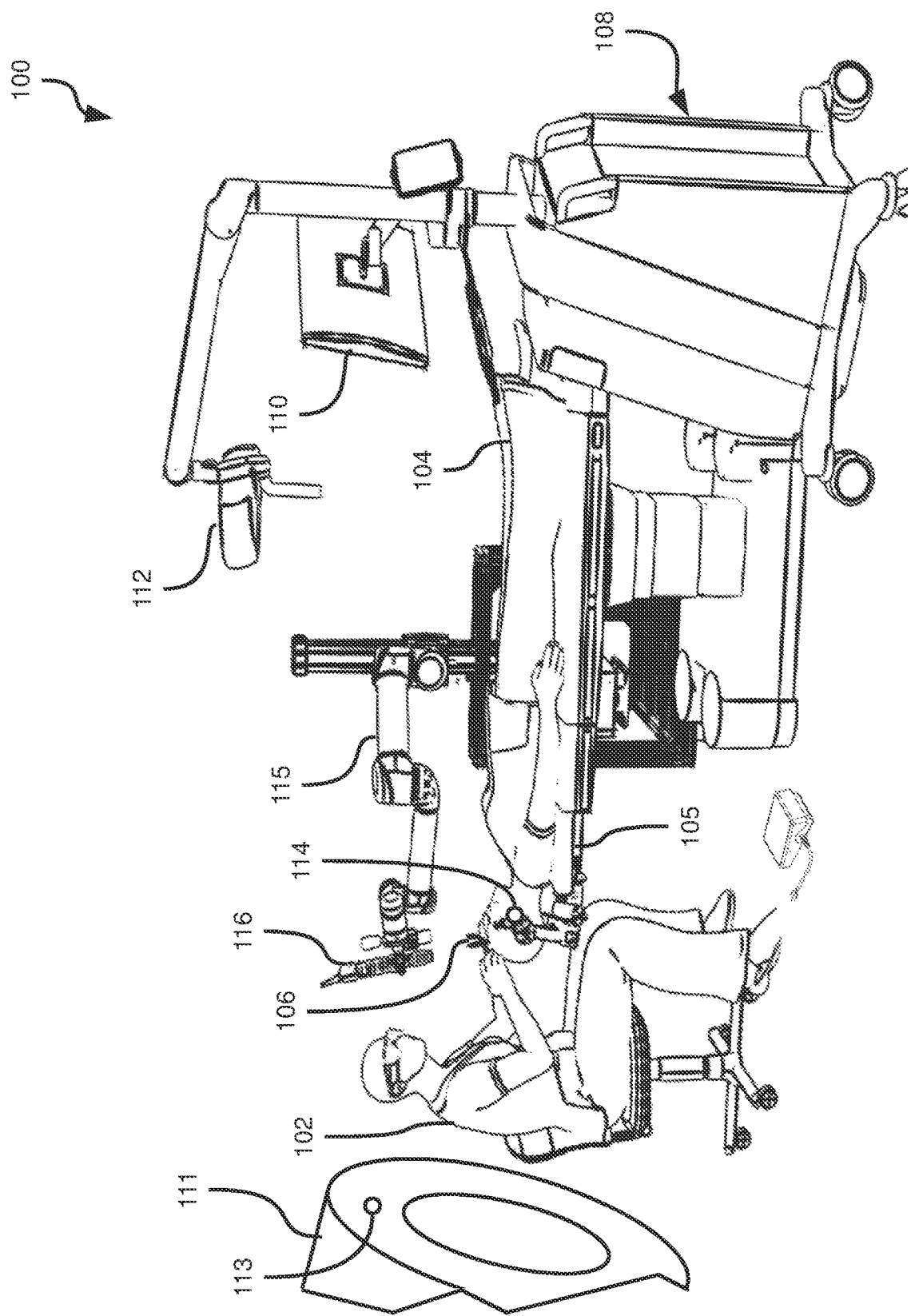
FIG. 1 depicts an operating theatre including a medical imaging system, according to a non-limiting embodiment.

Referring to FIG. 1, this diagram illustrates depicts a surgical operating theatre 100 in which a healthcare worker 102, e.g. a surgeon, operates on a patient 104 lying on a bed 105, in accordance with an embodiment of the present disclosure. Specifically, the surgeon 102 conducts a minimally invasive surgical procedure on the brain of the patient 104. Minimally invasive brain surgery involves the insertion and manipulation of instruments into the brain through an opening that is significantly smaller than the portions of skull removed to expose the brain in traditional brain surgery techniques. Surgical procedures, other than brain surgery, may also be performed in operating theatre 100 and make use of the systems and methods herein described.

Still referring to FIG. 1, the opening through which the surgeon 102 inserts and manipulates the instruments is provided by an access port 106. The access port 106 typically comprises a hollow cylindrical device with open ends. During insertion of the access port 106 into the brain (after a suitable opening has been drilled in the skull), an introducer (not shown) is generally inserted into the access port 106. The introducer is typically a cylindrical device that slidably engages an internal surface of the access port 106 and bears a conical atraumatic tip to allow for insertion of the access port 106 into the brain. Following insertion of the access port 106, the introducer may be removed; and the access port 106 may then enable insertion and bimanual manipulation of surgical tools into the brain. Examples of such tools comprise suctioning devices, scissors, scalpels, cutting devices, imaging devices, e.g. ultrasound sensors, and the like.

Still referring to FIG. 1, an equipment tower 108 supports a computing device (not shown), such as a desktop computer, as well as one or more displays 110 connected to the computing device for displaying images provided by the computing device. The images provided to the display 110 from the computing device comprise images captured by a medical imaging device 111, which, in the present embodiment, comprises an MRI scanner (only partially visible in FIG. 1). A variety of other imaging devices are also contemplated, including, for example, computed tomography (CT) scanners and the like. The device 111 is employed to capture images of the patient 104 both before and during the medical procedure. To capture such images, the patient 104 is repositioned (either by moving the bed 105 or by placing the patient 104 on another bed or gantry (not shown) in proximity with the device 111 (for example, to place the head of the patient 104 within the bore of the MRI scanner).

Still referring to FIG. 1, the equipment tower 108 also supports a tracking system 112. An example of the tracking system 112 is the Polaris ° system available from Northern Digital Inc. The tracking system 112 is generally configured to track the positions of one or more fiducial markers mounted on any of the above-mentioned equipment. The tracking system 112 comprises a camera, e.g. a stereo camera, and a computing device (either the same device as above mentioned or a separate device) configured to locate the fiducial markers in images captured by the camera and determine the spatial positions of the markers.

Still referring to FIG. 1, the nature of the markers and the camera are not particularly limited. For example, the camera may be sensitive to infrared (IR) light; and the tracking system 112 comprises one or more IR emitters, e.g. IR light emitting diodes (LEDs, to shine IR light on the markers. In other examples, marker recognition in the tracking system 112 is based on radio frequency (RF) radiation, visible light emitted from devices, such as pulsed or un-pulsed LEDs, electromagnetic (EM) radiation other than IR or visible light, and the like. For RF-based tracking and EM-based tracking, each object is fitted with markers having signatures unique to that object; and the tracking system 112 comprises antennae rather than the above-mentioned camera. Combinations of the above elements may also be employed.

Still referring to FIG. 1, each tracked object generally comprises three or more markers fixed at predefined locations on the object. Example markers 113 and 114 are respectively affixed to the MRI scanner 111 and the patient 104, although single markers are illustrated only for simplicity. In practice, each of the MRI scanner 111 and the patient 104 are provided with an array of markers. The predefined geometries of the marker arrays and the locations of markers within the arrays are configured within the tracking system 112. Thus, the tracking system 112 is configured to capture images of operating theatre 100, and compare the positions of any visible markers to the preconfigured geometry and marker locations. Based on the comparison, the tracking system 112 determines which marker arrays are present in the field of view of the camera, as well as in which positions those objects are currently disposed. The tracking system 112, therefore, enables tracking of the position of the patient 104 and the MRI scanner 111, themselves, by detecting the location and the position of the marker arrays disposed at fixed positions relative to each of the patient 104 and the MRI scanner 111. The tracking of the patient 104 and imaging device positions is below further described in greater detail.

Still referring to FIG. 1, an automated articulated arm 115, also referred to as a robotic arm, carries an external scope 116, e.g., external to patient 104. The external scope 116 is positioned over the access port 106 by the robotic arm 115, and captures images of the brain of the patient 104 (or any other portion of the patient 104, depending on the nature of the medical procedure being performed) for presentation on the display 110. The movement of the robotic arm 115 to place the external scope 116 correctly over the access port 106 may be guided by the tracking system 112 and the computing device in the equipment tower 108. The images from the external scope 116, presented on the display 110, is overlaid with other images, including images obtained prior to the surgical procedure. The images presented on the display 110 may also display virtual models of surgical instruments present in the field of view of the tracking system 112 (the positions and orientations of the models having been determined by the tracking system 112 from the positions of marker arrays, as above mentioned).

Still referring to FIG. 1, the medical procedure, e.g., the above-mentioned minimally invasive surgical procedure, such as a tumor resection, performed on the patient 104 typically requires that the patient 104 be on the bed 105. Tracking position of the patient 104 is enabled by affixing a marker array (the marker 114) directly to the patient 104, to the bed 105, or to an intermediate structure, such as a head holder fixing the skull of the patient 104 to the bed 105. During the procedure, acquiring one or more intraoperative images of the patient 104 using the MRI scanner 111 (or any other suitable imaging device) may be necessary. The patient 104 must, therefore, be repositioned from the bed 105 onto a gantry (not shown) associated with the MRI scanner 111. The bed 105, itself, may also be repositioned to place the patient 104 within the MRI scanner 111. Once the patient 104 has been repositioned, instructions are provided, e.g. by the above-mentioned computing device, to the MRI scanner 111 to capture one or more images of the patient 104. Such instructions may be required to specify the position of the patient 104 relative to the MRI scanner 111, as below discussed in greater detail.

Still referring to FIG. 1, when the intraoperative image or below images have been acquired, below patient 104 is repositioned again, substantially returning to the position shown, for continuation of the medical procedure. The repositioning of below patient 104 presents challenges in maintaining the tracked position of below patient 104, as below discussed.

Figure 2A:
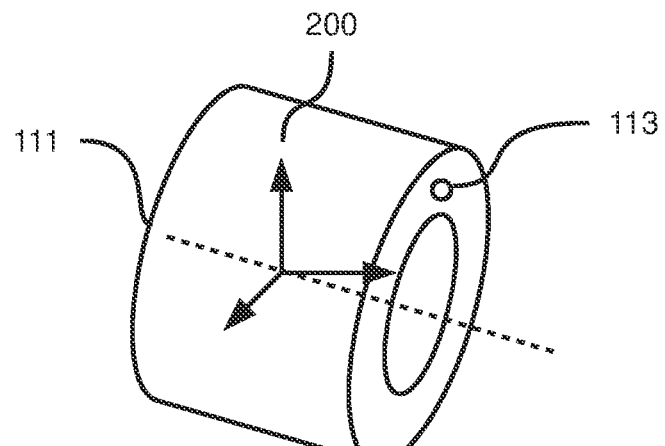
FIGS. 2A-2C depicts various frames of reference at use in the medical imaging system of FIG. 1, according to a non-limiting embodiment.
Figure 2B:
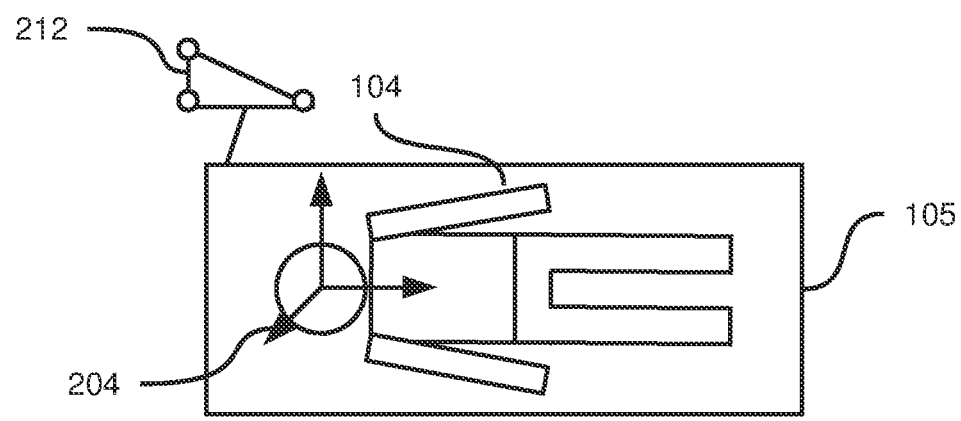
Figure 2C:
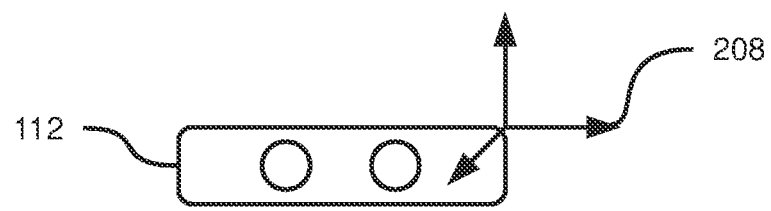

Referring to FIGS. 2A-2C, together, these diagrams illustrate various frames of reference employed in an operating theatre 100, in accordance with some embodiments of the present disclosure. Referring to FIG. 2A, this diagram illustrates an MRI scanner 111, for example, employs a frame of reference 200 (FIG. 2A) that establishes a coordinate system having an origin at a known location within the MRI scanner 111, in accordance with an embodiment of the present disclosure. Instructions to the MRI scanner 111, such as instructions to capture an image, generally identify a target location within the MRI scanner 111 in the frame of reference 200. That is, an instruction to the MRI scanner 111 identifies a location that is at a specified distance along each of three axes from the origin of the frame of reference 200. The origin may be the isocenter of the magnet in the MRI scanner 111, or any other predefined location within the MRI scanner 111. The capture instructions may also identify the orientation of the patient 104, in the frame of reference 200, to configure the imaging parameters employed by the MRI scanner 111, e.g., if a patient is supine, different imaging parameters are employed than if the patient is prone.

Referring to FIG. 2B, this diagram illustrates a patient frame of reference 204, by which locations within patient 104 are identified, in accordance with an embodiment of the present disclosure. For example, if an image of a certain portion of patient 104 is desired, that portion is originally identified by a specified distance along each of three axes from an origin at a known location on patient 104. The origin may be at a predefined anatomical location, and the axes may be defined in a variety of ways. Conventionally, the axes are defined by the intersections of the sagittal, coronal and transverse planes. The axes may be referred to, for example, as the Left (intersection of coronal and transverse planes), Posterior (intersection of sagittal and transverse planes) and Superior (intersection of sagittal and coronal planes) axes (LPS).

Referring to FIG. 2C, this diagram illustrates a tracking system frame of reference 208, in accordance with an embodiment of the present disclosure. The frame of reference 208 has an origin at a known location within the operating theatre 100 (that is, within the field of view of the camera of the tracking system 112). Coordinates within the frame of reference 208, thus, define locations within the operating theatre 100, independently of the patient 104 and the MRI scanner 111. Locations of marker-equipped tools are determined by the tracking system 112 in the frame of reference 208. In addition, to track the position of the patient 104, the tracking system 112 typically does not directly track the patient 104, but, instead, tracks a marker array, such as the array 212, as shown in FIG. 2B. Either the tracking system 112 or the computing device, above mentioned, store a fixed relationship between the position of the array 212 and the position of the frame of reference 204. For example, the relationship is stored as a vector from the current position of the array 212 to the origin of the frame of reference 204, along with orientations of the axes of the frame of reference 204.

Still referring to FIGS. 2A-2C, together, the above relationship is established by affixing the array 212 relative to the patient 104, and then employing a tracked pointer or other instrument to point to known locations on the patient 104 (such as the origin of the frame of reference 204). The vector defining the position of the patient 104 relative to the array 212 is stored in the memory; and, thereafter, by detecting the array 212, is be determined by storing another vector defining the position of the frame of reference 200 relative to the marker 113 (or an array of markers, not shown).

Still referring to FIGS. 2A-2C, together, during the above-mentioned repositioning of the patient 104 to acquire intraoperative images, often necessary is removing the array 212, e.g., as the array 212 does not fit within the bore of the MRI scanner 111. Therefore, the tracking system 112 is unable to track the position of the patient 104 as the patient 104 is repositioned within the MRI scanner 111. Further, following image acquisition, the array 212 is re-affixed to the patient 104, the bed 105, or the like. However, the position of the array 212 is unlikely to exactly coincide with the original position in connection with which the patient 104 registration was established. Therefore, the stored vector, defining the spatial relationship between frame of the reference 204 and the array 212, may be invalid.

Still referring to FIGS. 2A-2C, together, and ahead to FIG. 3, as below described, the computing device in the equipment tower 108 is configured to perform various actions that facilitate the maintenance or the recovery of the patient registration following the removal or the replacement of the array 212. Before a discussion of the functionality of the computing device, a brief description of the components of the computing device are provided.

Figure 3:
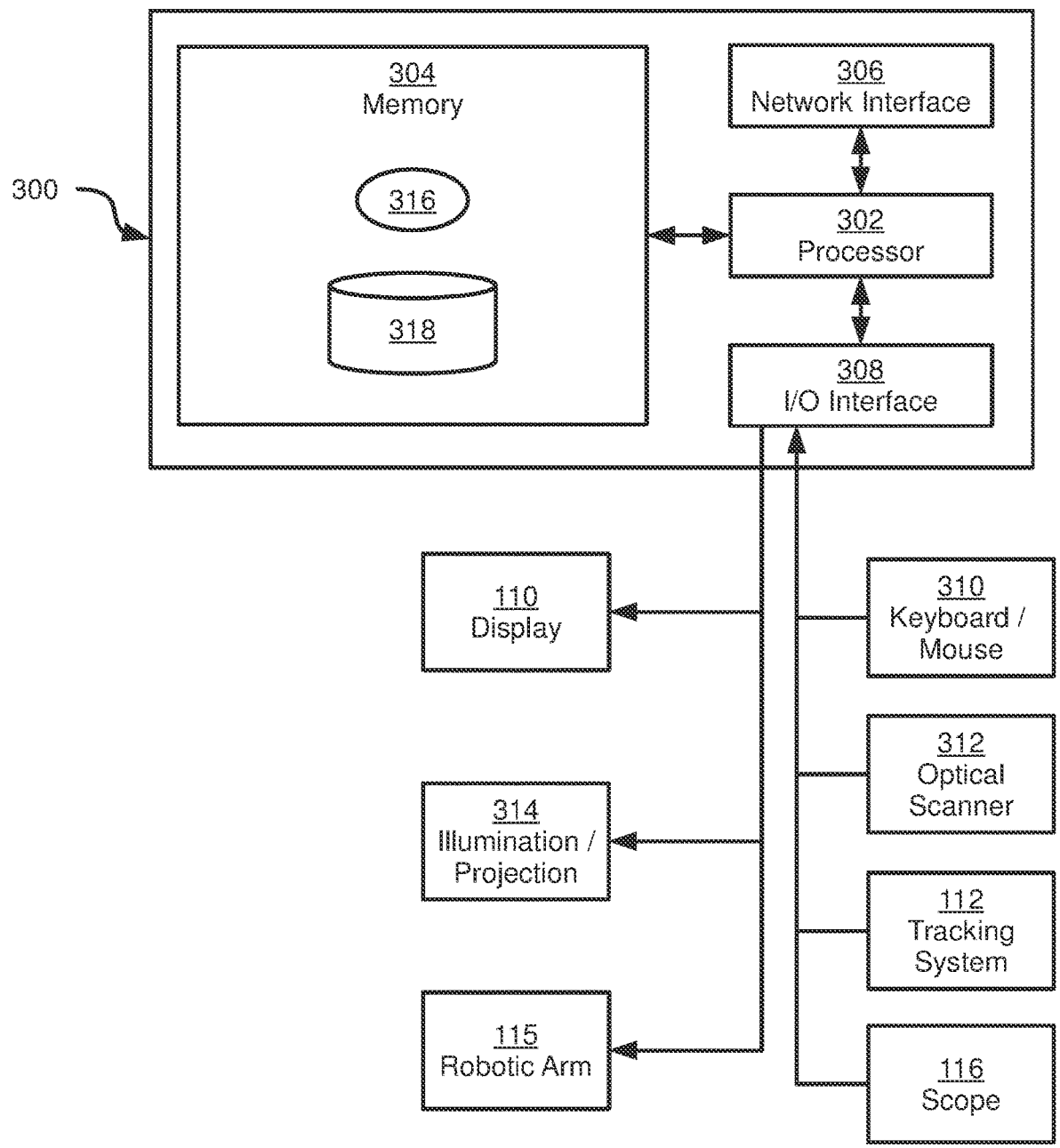
FIG. 3 depicts certain components of a computing device as implemented in the medical imaging system of FIG. 1, according to a non-limiting embodiment.

Referring to FIG. 3, this diagram illustrates a computing device 300, comprising a central processing unit (CPU, also referred to as a microprocessor or, simply, a processor) 302 interconnected with a non-transitory computer readable storage medium, such as a memory 304, in accordance with an embodiment of the present disclosure. The processor 302 and the memory 304 generally comprise one or more integrated circuits (ICs) and a variety of structures, for example, more than one CPU can be provided. The memory 304 comprises any suitable combination of volatile memory, e.g., Random Access Memory ("RAM"), and non-volatile, e.g., read only memory ("ROM"), Electrically Erasable Programmable Read Only Memory ("EEPROM"), flash memory, magnetic computer storage device, or optical disc. In the present example, the memory 304 comprises both a volatile memory and a non-volatile memory. Other types of non-transitory computer readable storage medium are also contemplated, such as compact discs, e.g., CD-ROM, CD-RW, and digital video discs (DVD).

Still referring to FIG. 3, the computing device 300 further comprises a network interface 306 interconnected with the processor 302. The network interface 306 allows the computing device 300 to communicate with other computing devices via a network, e.g., a local area network (LAN), a wide area network (WAN), or any suitable combination thereof. The network interface 306, thus, comprises any necessary hardware, e.g., radios, network interface controllers (NICs), and the like, for communicating over such networks. The computing device 300 further comprises an input/output interface 308, comprising the necessary hardware for interconnecting the processor 302 with various input and output devices. The interface 308 comprises, among other components, a Universal Serial Bus (USB) port, an audio port for sending and receiving audio data, a Video Graphics Array (VGA), Digital Visual Interface (DVI) or other port for sending and receiving display data, and any other suitable components.

Still referring to FIG. 3, via the interface 308, the computing device 300 is connected to input devices, including a keyboard, and a mouse 310, an optical scanner 312, e.g., a laser-based depth scanner configured to generate point cloud data, as well as an external scope 116, and the tracking system 112, above mentioned. Also via the interface 308, the computing device 300 is connected to output devices, including illumination or projection components 314, e.g., lights, projectors, and the like, as well as the display 110, the robotic arm 115, above mentioned, and other output devices, e.g., speakers, as well as to input devices, e.g., touch screens. The I/O interface 308 may be omitted entirely in some embodiments, or may be used to connect to only a subset of the devices, above mentioned. The remaining devices, or all devices, if the I/O interface 308 is omitted, may be connected to the computing device 300 via the network interface 306.

Still referring to FIG. 3, the computing device 300 stores, in the memory 304, a registration maintenance application 316 (also referred to herein as application 316) comprising a plurality of computer readable instructions executable by the processor 302. When the processor 302 executes the instructions of the application 316 (or, indeed, any other application stored in the memory 304), the processor 302 performs various functions implemented by those instructions, as below discussed. The processor 302, or the computing device 300 more generally, is, therefore, said to be "configured" or "operating" to perform those functions via the execution of the application 316.

Still referring to FIG. 3, also stored in the memory 304 are various data repositories, including a patient data repository 318. The patient data repository 318 contains a surgical plan defining the various steps of the minimally invasive surgical procedure to be conducted on the patient 104, as well as image data relating to the patient 104, such as images captured using the MRI scanner 111. The repository 318 also contains patient registration information, such as the above-mentioned vectors defining the spatial relationship between the patient 104 and the array 212. As above mentioned, the computing device 300 is configured, via the execution of the application 316 by the processor 302, to perform various actions related to facilitating the maintenance or recovery of the patient registration. Those functions are below further described in detail.

Figure 4:
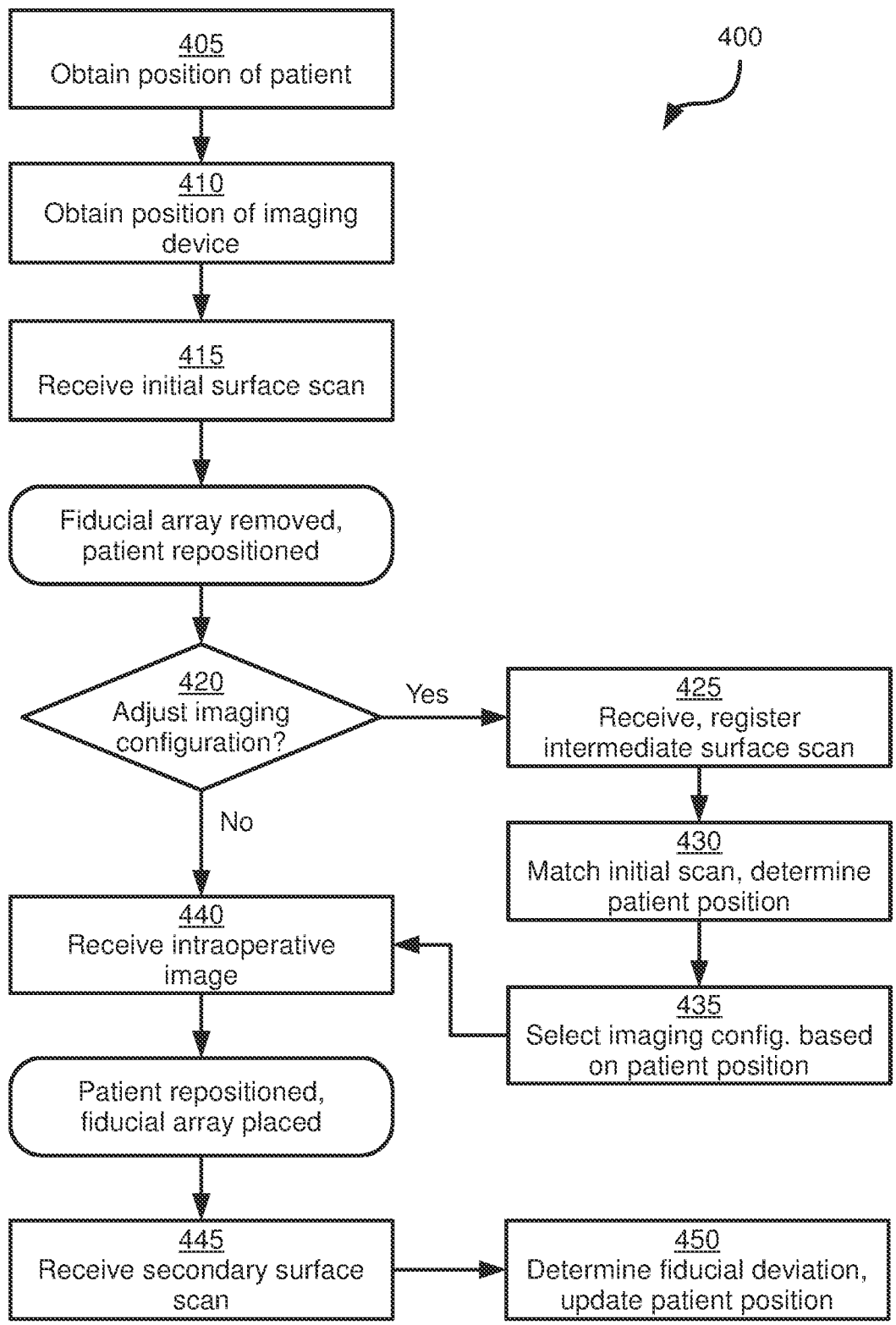
FIG. 4 depicts a method of transferring patient registration in the medical imaging system of FIG. 1, according to a non-limiting embodiment.

Referring to FIG. 4, this flow diagram illustrates a method 400 of maintaining patient registration is depicted, in accordance with an embodiment of the present disclosure. The method 400 is described in conjunction with its steps performed via the computing device 300, as deployed in operating theatre 100. The method 400 is implemented on other computing devices in other systems. Beginning at block 405, the computing device 300 is configured to obtain the position of the patient 104. The position, obtained at block 405, is obtained within the frame of reference 208. That is, the location of the patient 104 is obtained as coordinates within the frame of reference 208, representing the location of the origin of the patient frame of reference 204 (and, optionally, vectors indicating the orientations of the axes of the frame of reference 204 within the frame of reference 208). The position of the patient 104 is obtained via detection, by the tracking system 112, of the location and the orientation of the marker array 212, and the application of the stored patient registration vector data (mentioned earlier) to that location and that orientation. The position may be obtained by the computing device 300 via receipt from the tracking system 112, or the position may be obtained by the computing device 300 by assisting the tracking system 112 in the determination of the position. For instance, the computing device 300 may: receive raw image data from the tracking system 112, identify the array 212 within the raw data, and apply the patient registration vector data.

Still referring to FIG. 4, at block 410, the computing device 300 is configured to obtain the position of an imaging device, such as the MRI scanner 111. As in block 405, the position, obtained at block 410, is obtained within the frame of reference 208 (that is, the physical location of the MRI scanner 111 within the operating theatre 100). The position of the MRI scanner 111 within the operating theatre 100 may be obtained from the tracking system 112. The tracking system 112, either independently or in conjunction with the computing device 300, is configured to detect the marker 113 (and any other markers affixed to the MRI scanner 111) and, based on the positions of such markers and a stored model of the geometry of the MRI scanner 111 (or the geometry of a marker array affixed to the MRI scanner 111 in combination with a registration vector), determine the position and the orientation of the MRI scanner 111 within the operating theatre 100. Blocks 405 and 410 can be substantially simultaneously performed. That is, the tracking system 112 captures an image that encompasses both the array 212 and the marker 113; and, based on that image, determine both of the above-mentioned positions. The positions, obtained at blocks 405 and 410, are stored in the memory 304.

Still referring to FIG. 4, at block 415, the computing device 300 is configured to receive, for example, via the interface 308, an initial surface scan depicting the patient 104 and the array 212 in a first position (that is, in the position in which the array 212 appeared at block 405). For example, the surface scan may depict the patient 104 and the array 212, as shown in FIG. 2B. The nature of the surface scan is not particularly limited. In the present embodiment, the surface scan is received as point cloud data from the optical scanner 312, comprising a handheld optical scanner. For example, the optical scanner 312 comprises one or more laser emitters and one or more light sensors for measuring the depth (relative to the scanner itself) of a plurality of points in the field of view of the scanner. The point cloud data, received at block 415, therefore, comprises, for each of a plurality of points (some representing at least a portion of patient 104, and some representing array 212), a three-dimensional position in a scan frame of reference distinct from any of the frames of reference described in connection with FIGS. 2A-2C.

Figure 5:
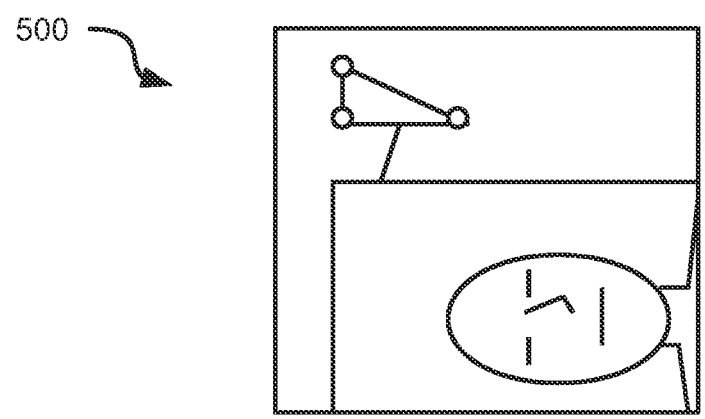
FIG. 5 depicts an initial surface scan received by the computing device of the system of FIG. 1 during the performance of the method of FIG. 4.

Referring to FIG. 5, this diagram illustrates an example initial surface scan 500, in accordance with an embodiment of the present disclosure. Referring to FIG. 5 and referring back to FIGS. 3 and 4, understood is that the point cloud data, received from scanner 312, need not be graphical data, but, rather, is illustrated as such. In some embodiments, the performance of block 415 can include the registration of the surface scan data to the tracking system frame of reference. For example, the computing device 300 is configured to detect the points in the surface scan corresponding to the array 212. Since the position of the array 212 in the tracking system frame of reference 208 is known, the computing device 300 can register the detected points to the frame of reference 208. Further, since the point cloud data itself indicates the position of each point relative to other points, once the points depicting the array 212 have been registered, the remaining points can also be registered, for example, by assigning a set of coordinates in frame of reference 208 to each point in the surface scan.

Figure 6:
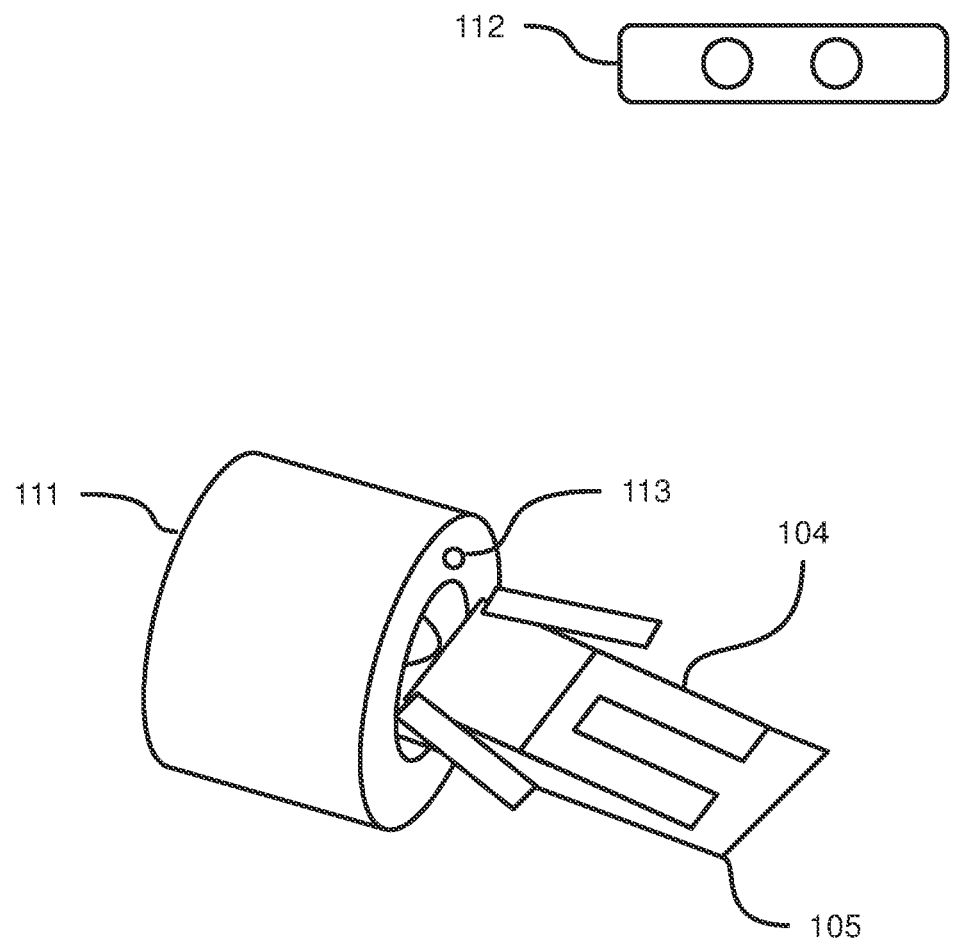
FIG. 6 depicts the patient and medical imaging device of the system of FIG. 1, arranged to capture an intraoperative image, according to a non-limiting embodiment.

Referring to FIG. 6, this diagram illustrates that, following the receipt of the initial surface scan, and typically following a portion of the medical procedure, the patient 104 is repositioned for acquisition of an intraoperative image, in accordance with an embodiment of the present disclosure. In FIG. 6 and referring back to FIG. 1, in the present example, the patient 104 is repositioned from the position, as shown in FIG. 1, to a position, as shown in FIG. 6, with the head of the patient 104 placed within the bore of MRI scanner 111. In FIG. 6 and referring back to FIGS. 2B, 3, and 5, the bore of the MRI scanner 111 provides insufficient space to accommodate the array 212; and the array 212 has, therefore, been removed. As a result, the camera of the tracking system 112 no longer tracks the position of array 212; and the computing device 300 no longer obtains the position of the patient 104.

Still referring to FIG. 6 and referring back to FIGS. 3 and 4, following the repositioning of the patient 104, the computing device 300 is configured to determine whether to adjust the imaging configuration for the MRI scanner 111. The determination, at block 420, is made by the receipt of input data from an operator of the computing device 300, indicating whether or not adjustment is required. In other embodiments, the computing device 300 is configured to omit the determination, at block 420, and either always performs the tasks, as shown in FIG. 4, as following a "yes" determination, or always performs the tasks illustrated as following a "no" determination.

Still referring to FIG. 6 and referring back to FIGS. 2 and 4, the MRI scanner 111 employs magnetic gradients that are intended to align with various axes of the patient 104. That is, a default configuration of the MRI scanner 111 assumes a certain relationship between the frame of reference 200 and the frame of reference 204. For example, the default configuration assumes that the superior axis of the frame of reference 204 is parallel to the axis of the bore of the MRI scanner 111. Minor deviations in patient position, e.g., a deviation of below ten degrees between the patient superior axis and the bore axis, may have little or no effect on the resulting image acquired by the MRI scanner 111. However, greater deviations may negatively impact the fidelity of images acquired by MRI scanner 111. Therefore, adjusting the orientation of the above-mentioned gradients, based on the position of the patient 104 in the MRI scanner 111, by making an affirmative determination, at block 420, is advantageous.

Still referring to FIG. 6 and referring back to FIGS. 2-4, following an affirmative determination, at block 420, the computing device 300 proceeds to block 425. At block 425, the computing device 300 is configured to receive an intermediate surface scan. As with the initial surface scan, the intermediate surface scan defines point cloud data; however, the intermediate scan depicts a portion of the patient 104 (at least partially overlapping with the portion depicted in the initial scan) as positioned within the MRI scanner 111, and does not depict the array 212. The intermediate surface scan, in the present embodiment, is comprises the scanner 312 (that is, the MRI scanner 111 comprises a mounting structure for accepting the scanner 312 in a fixed, known, position within the bore or the optical scanner comprises a different scanner than the device from which the initial scan data was received).

Figure 7A:
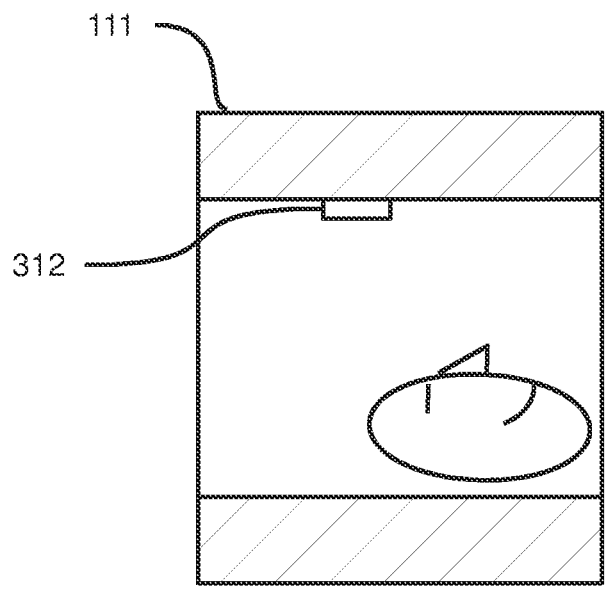
FIG. 7A depicts the patient of FIG. 1 repositioned for acquisition of an intraoperative image, according to a non-limiting embodiment.

Referring to FIG. 7A, this diagram illustrates the patient 104 within the bore of the MRI scanner 111, as well as the optical scanner 312 mounted within the bore of the MRI scanner 111, in accordance with an embodiment of the present disclosure.

Figure 7B:
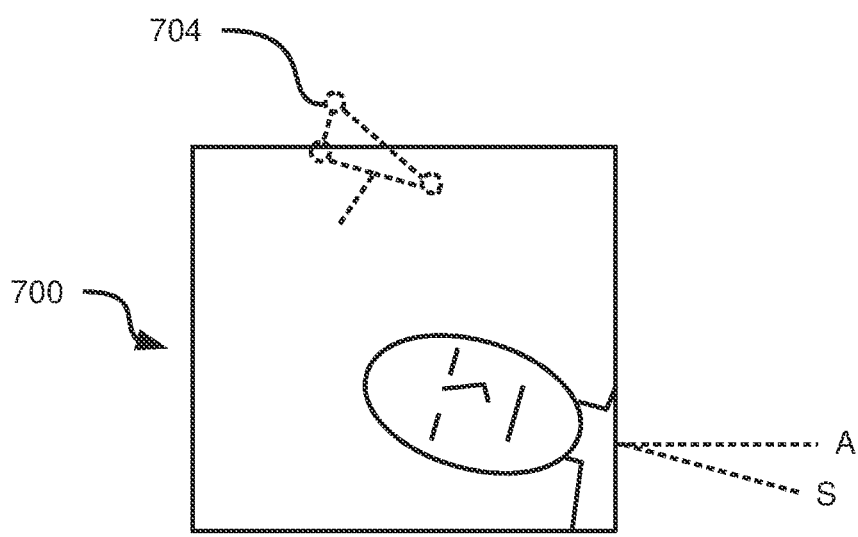
FIG. 7B depicts an intermediate surface scan acquired in the position shown in FIG. 7A, according to a non-limiting embodiment.

Referring to FIG. 7B, this diagram illustrates an intermediate surface scan 700, acquired by the scanner 312, in the position, as shown in FIG. 7A, in accordance with an embodiment of the present disclosure.

Referring back to FIG. 4, at block 425, the intermediate surface scan is also registered to the tracking system frame of reference 208. Registration of scan 700 to frame of reference 208 is accomplished by use of the position of the MRI scanner 111, obtained at block 410, along with the known position of the optical scanner 312 relative to the MRI scanner 111.

Referring back to FIGS. 7A and 7B, together, and referring back to FIGS. 2, 4, and 5, the position of the patient 104 cannot be directly derived from the scan 700, even once the scan 700 has been registered in the frame of reference 208. Instead, at block 430, the computing device 300 is configured to register the intermediate scan 700 and the initial scan 500 to a common frame of reference, e.g., the frame of reference of scan 700, and, based on that registration, determine a virtual position for the array 212. That is, the computing device 300 is configured to match the depictions of the patient 104 in the scans 500, 700 (by any suitable image registration technique), and, based on the position of the array 212 in the scan 500, to determine where the array 212 would appear in the scan 700 if the array 212 was present in the field of view of the scanner 312.

Referring back to FIG. 7B, a virtual depiction 704 of the array 212 indicates where, in the scan 700, that the array 212 would be depicted if the array 212 had been present. Because the scan 700 is registered to the frame of reference 208, once the virtual position of the array 212 within the scan 700 is established, the virtual position of array 212 in the frame of reference 208 can be determined. As a result, by applying the previously mentioned patient registration vector data, the computing device 300 can conclude the performing the step of block 430 by determining the position of the patient 104 in the frame of reference 208, despite the physical absence of the array 212.

Still referring back to FIG. 7B and referring back to FIG. 4, at block 435, having determined the position of the patient 104, and having previously obtained the position of the MRI scanner 111, the computing device 300 is configured to automatically select an imaging configuration for the MRI scanner 111 based on a comparison of the position of the patient 104 and the position of the MRI scanner 111. For example, the computing device 300 is configured to determine a deviation between the actual position of the patient 104, e.g., of the frame of reference 204, and the default, or expected, position of the patient 104 for the MRI scanner 111. The superior axis S of the patient 104 is disposed at an angle of approximately fifteen degrees relative to the axis A of the bore of the MRI scanner 111. The deviation may include any combination of rotations and translations and can be determined based on any suitable conventional algorithm. The imaging configuration, selected at block 435, can also include an imaging volume, e.g., the size of the space to be imaged.

Still referring back to FIG. 7B and referring back to FIG. 4, the default gradients for MRI scanner 111 may be configured assuming that axis S is parallel with axis A. Therefore, at block 435, the computing device 300 may select an imaging configuration that modifies the gradients to accommodate the actual orientation of the patient 104. The selection can include a computation of gradient alignments, e.g., in frame of reference 200, or the selection can include simply communicating the above-mentioned deviation to the MRI scanner 111, which, itself, can be configured to select the appropriate modified gradients.

Referring back to FIG. 4, having selected an imaging configuration at block 435, the computing device 300 is configured to continue the performance of method 400 at block 440. Alternatively, if the determination, at block 420, is negative, the performance of blocks 425-435 is omitted; and the computing device 300 proceeds directly to block 440, without modifying the default imaging configuration for the MRI scanner 111. At block 440, the computing device 300 is configured to receive an intraoperative image of the patient 104 from the MRI scanner 111. The intraoperative image is received, via the interface 308 or the network interface 306, and is stored in the repository 318. In some embodiments, the computing device 300, itself, is configured to the control MRI scanner 111 to acquire the intraoperative image. In other embodiments, however, the MRI scanner 111 is directly controlled by an operator, or by a distinct computing device; and the computing device 300 simply receives the resulting image(s).

Still referring back to FIG. 4 and referring back to FIGS. 1 and 2B, following acquisition of the intraoperative image, the patient 104 is removed from the MRI scanner 111 and returned to substantially the position, as shown in FIG. 1, for continuation of the medical procedure. The array 212 is also replaced; however, the location of the array 212 may not be identical to its original location, as shown in FIG. 2B. In other words, the patient registration vector data, defining the position of the frame of reference 204 relative to the tracked position of the array 212 in the frame of reference 208 may no longer be accurate. In order to reduce or eliminate the need to repeat a time-consuming manual patient registration process, the computing device 300 is configured, at block 445, to receive a secondary surface scan, e.g., from a handheld optical scanner, such as the scanner 312, having been removed from the MRI scanner 111. The secondary scan depicts at least a portion of the patient 104 (at least partially overlapping with the portion depicted in the initial surface scan), as well as the array 212 in a second position.

Figure 8A:
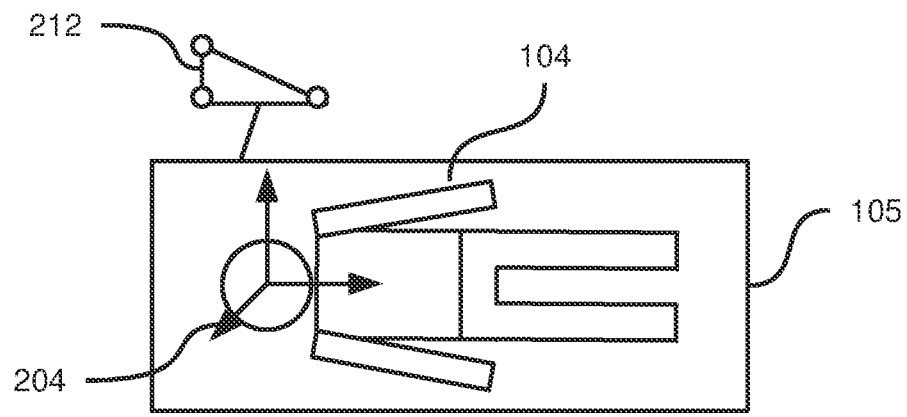
FIG. 8A depicts the patient of FIG. 1, repositioned for continuation of a medical procedure, following acquisition of an intraoperative image, according to a non-limiting embodiment.

Referring to FIG. 8A, this diagram illustrates the patient 104 with the array 212 reaffixed to the bed 105 in a different position than that shown in FIG. 2B, in accordance with an embodiment of the present disclosure.

Figure 8B:
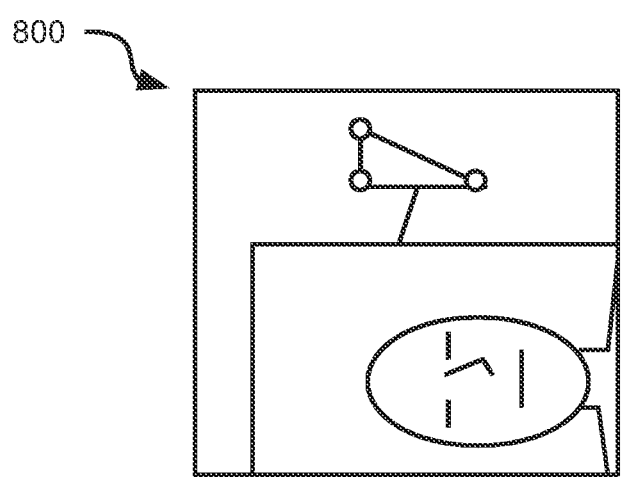
FIG. 8B depicts a secondary surface scan acquired in the position shown in FIG. 8B, according to a non-limiting embodiment.

Referring to FIG. 8B, this diagram illustrates a secondary scan 800, depicting the head of the patient 104 on the bed 105, as well as the array 212 in its second position (farther from the head of the bed 105 than the first position of the array 212), in accordance with an embodiment of the present disclosure.

Referring to FIGS. 8A and 8B, together, and referring back to FIG. 4, at block 450, having received the secondary surface scan, the computing device 300 is configured to detect a deviation in the position of the array 212 relative to the patient 104 between the initial surface scan 500 and the secondary surface scan 800. More specifically, the computing device 300 is configured to: register the scans 500, 800 to a common frame of reference, based on the point cloud data depicting the patient 104, to identify the remainder of the point cloud data depicting the array 212 in each scan, and determine a deviation, e.g., a translation, a rotation, a scaling, and the like, between the depiction of the array 212 in the scan 500 and the depiction of the array 212 in the scan 800.

Figure 9:
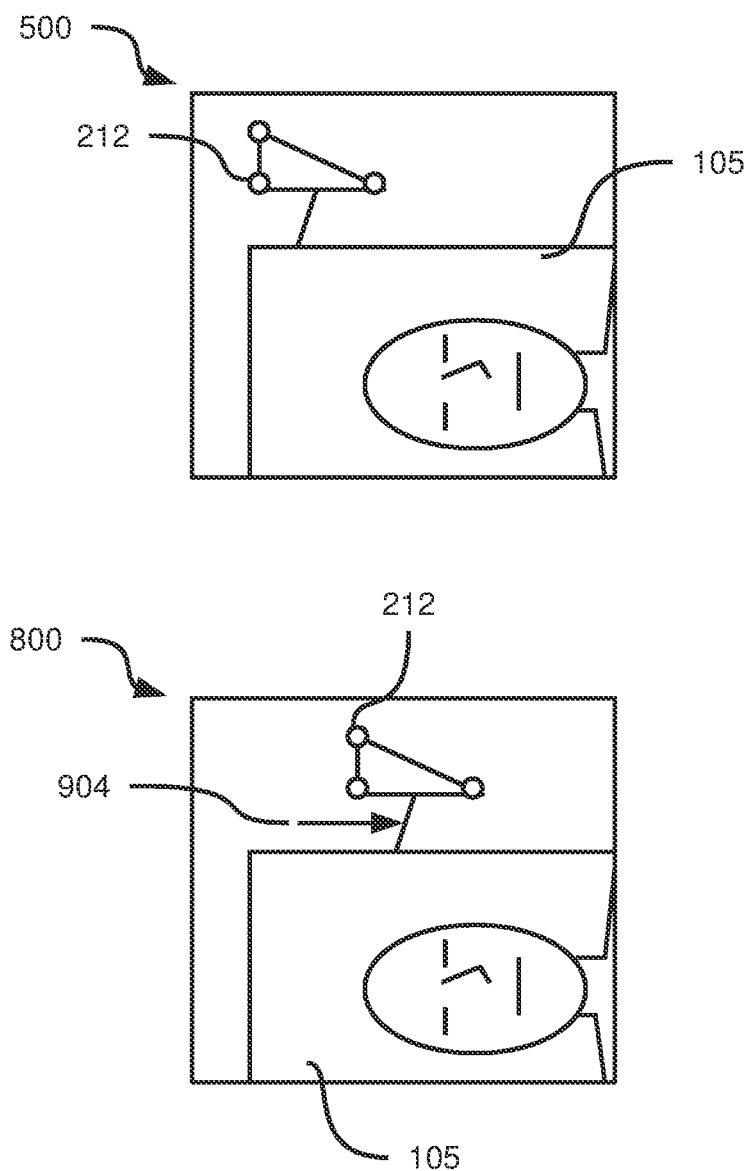
FIG. 9 depicts a deviation in the position of a marker array affixed to the patient of FIG. 1.

Referring to FIG. 9, this diagram illustrates the scans 500, 800, as shown in FIGS. 8A and 8B, and a deviation 904, in the form of a translation, indicating that the array 212, in the second position, is a certain distance farther from the head of the bed 105 than in the first position, in accordance with an embodiment of the present disclosure. Following determination of the deviation 904, the computing device 300 is configured to apply the deviation 904 to the patient registration vector that is previously stored in the memory 304, for generating an updated patient registration vector from which an updated patient position is obtained based on the position of the array 212 in the frame of reference 208. In such a manner, patient registration is maintained without the need to repeat a manual registration process to generate a new registration vector.

Still referring to FIG. 9, in other embodiments, the computing device 300 performs the step, at block 450, without registering the scans 500, 800 to a common frame of reference. In such embodiments, the computing device 300 is configured to detect a predetermined set of anatomical features of the patient 104 in each of the scans 500, 800. For example, the computing device 300 stores image attributes in the memory 304, thereby permitting the computing device 300 to detect ears, eyes, and a nose of the patient 104. The computing device 300 is configured to detect such features in each of the scans 500, 800, and to determine vectors between the array 212 and those features in each of the scans. In other words, the computing device 300 determines a depicted position of the array 212 relative to the anatomical features in each scan. By comparing the depicted positions from the scans 500, 800, the computing device 300 is then configured to determine the above-mentioned deviation 904.

Still referring to FIG. 9, variations to the above systems and methods are contemplated. For example, although the surface scans mentioned above depict the patient 104, the scans may also depict other equipment affixed to patient 104. For example, in brain surgery, the head of the patient 104 is typically affixed to a head holder (not shown) to reduce or eliminate movement of the head during the procedure. The head holder is generally not removed until the procedure is complete; and, therefore, appears in surface scans. The features of the head holder may also be employed in registering each surface scan to one another.

Still referring to FIG. 9 and referring back to FIG. 4, in some embodiments, the steps of blocks 425-435 may be replaced with the capture of a scout intraoperative image which may be compared to an atlas image or a preoperative image of the patient 104 depicting the expected (or default) patient position within the MRI scanner 111. From that comparison, the deviation between the actual patient position and the expected patient position may be determined; and an imaging configuration may be selected for further intraoperative images.

Still referring to FIG. 9 and referring back to FIGS. 4 and 7A, in further embodiments, imaging configuration adjustment, at blocks 425-435, is achieved without reference to the initial surface scan, at block 415. For example, when the optical scanner 312 is mounted at a known position within the imaging device 111, as shown in FIG. 7A, the position of the scanner 312 (and therefore of any point cloud data generated by the scanner 312) relative to the frame of reference 200 is known. At block 425, a surface scan is captured by the scanner 312 and registered to the frame of reference 200 by virtue of the known fixed transformation between the scanner 312 and the frame of reference 200. Rather than comparing the scan, from block 425 to a previous scan, from block 425, can instead be compared to an atlas image having an anatomical alignment corresponding to the default configuration for the imaging device 111.

Still referring to FIG. 9 and referring back to FIG. 4, based on the comparison, the computing device 300 is configured to determine a transformation between the surface scan and the atlas; and the transformation indicates the actual position of the patient 104 relative to "expected" default patient position corresponding to the default imaging configuration of the imaging device 111. That transformation is then be employed to select an updated imaging configuration at block 435, as above described. In the above embodiment, if regaining patient registration with a tracking system is not required, e.g., when the image obtained at block 440 is a diagnostic image, rather than an intraoperative image, the steps of blocks 405-415 and 445-450 can be omitted.

Figure 10:
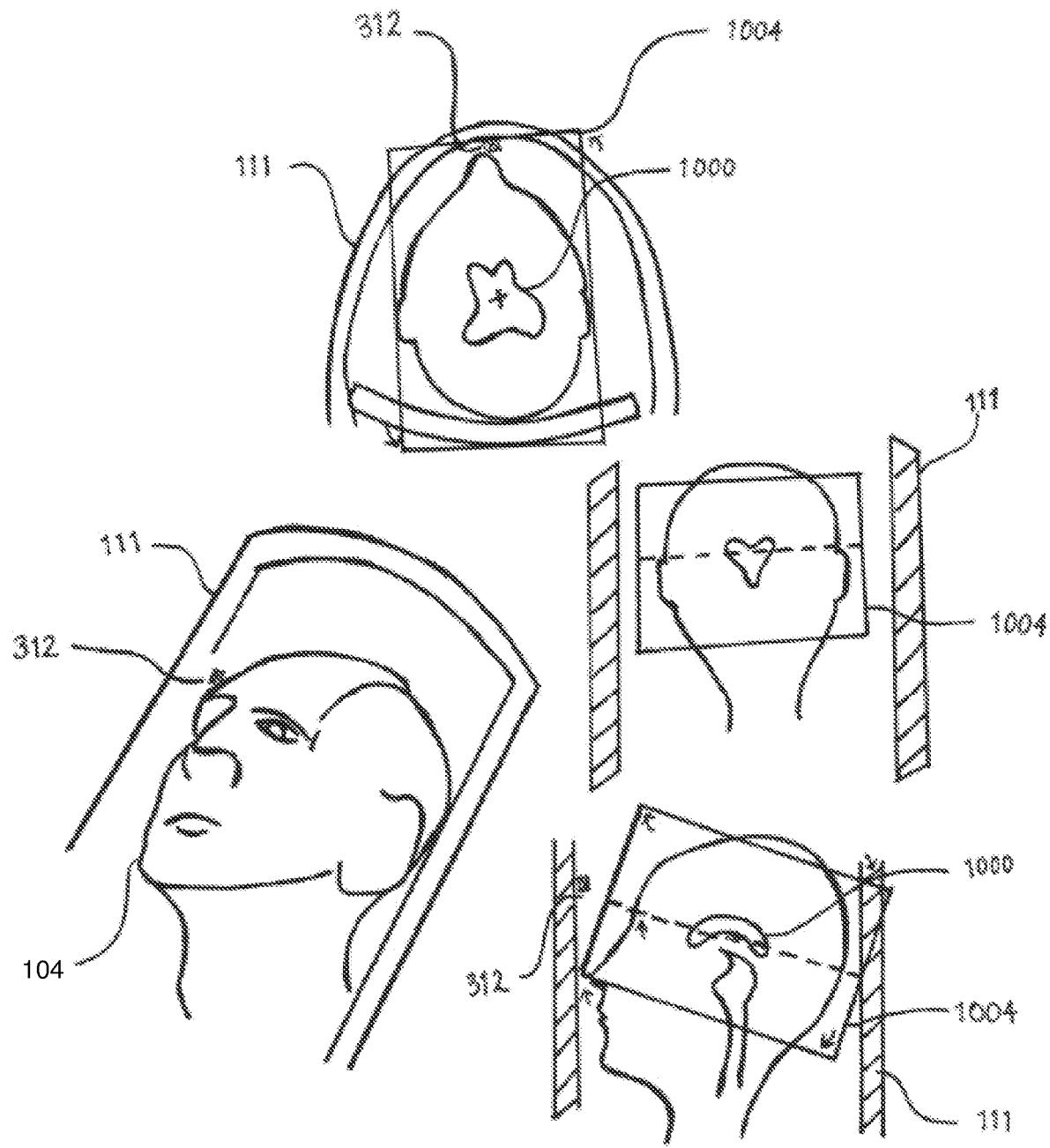
FIG. 10 depicts the generation of an adjusted imaging volume based on a surface scan of the patient of FIG. 1, according to a non-limiting embodiment.

Referring to FIG. 10, this diagram illustrates the generation of an adjusted imaging volume, based on a surface scan of the patient 104, as shown in FIG. 1, in accordance with an embodiment of the present disclosure. Similarly, as shown in FIG. 7A, the patient 104 is disposed within the imaging device 111, and the optical scanner 312 is affixed inside the bore of the imaging device 111 at a known position relative to the frame of reference 200. Responsive to receiving a surface scan from the scanner 312, the computing device 300 is configured to retrieve an atlas image from the memory 304 and to compare the point cloud data of the surface scan to the atlas image. For example, the computing device 300 is configured to receive input identifying a target tissue, e.g., the corpus callosum 1000, and to infer the position of the target tissue, based on the surface scan and the atlas image (which may depict both external surface and internal anatomical structures). From the inferred position of the target tissue within the patient 104, the computing device 300 is configured to determine a transformation to apply to the parameters defining an imaging volume 1004 of the imaging device 111, to center the imaging volume at a predefined angle on the target tissue.

Appreciated is that, in some embodiments, the functionality of the processor 302 and the application 316 may be implemented using pre-programmed hardware or firmware elements, e.g., application-specific integrated circuits (ASICs), electrically erasable programmable read-only memories (EEPROMs), etc., or other related components. The scope of the claims should not be limited by the embodiments set forth in the above examples, but should be given the broadest interpretation consistent with the description as a whole.

What is claimed:

1. A method of maintaining patient registration by way of a computing device comprising a processor, the method comprising:
    obtaining a position of a patient in a tracking system frame of reference based on a fiducial marker array affixed in a first position relative to the patient by the processor;
    receiving an initial surface scan of the patient and the fiducial marker array in the first position by the processor,
    receiving an intermediate surface scan of the patient prior to receiving an intraoperative image from a medical imaging device;
    determining a further position of the patient in the tracking system frame of reference based on a comparison of the intermediate surface scan and the initial surface scan by:
        registering the intermediate surface scan to the tracking system frame of reference,
        registering the initial surface scan to the intermediate surface scan,
        determining a virtual position for the fiducial marker array, and
        determining the further position of the patient, based on the virtual position based on the registration of the initial surface scan with the intermediate surface scan,
    obtaining a position of the medical imaging device in the tracking system frame of reference; and
    selecting an imaging configuration based on a comparison of the further position and the position of the medical imaging device.

2. The method of claim 1, further comprising:
    controlling the medical imaging device to capture the intraoperative image according to the imaging configuration; and
    responsive to capturing the intraoperative image of the patient by the medical imaging device:
        obtaining a position of the fiducial marker array affixed in a second position relative to the patient in the tracking system frame of reference;
        receiving a secondary surface scan of the patient and the fiducial marker array in the second position;
        detecting a deviation in a position of the fiducial marker array relative to the patient between the initial and secondary surface scans; and applying the deviation to the further position of the patient to generate an updated position of the patient in the tracking system frame of reference based on the fiducial marker array affixed in the second position.

3. The method of claim 2, wherein detecting the deviation comprises:
registering the initial and secondary surface scans to a common frame of reference based on the patient as depicted in each of the initial and secondary surface scans;
determining the deviation by comparing the positions of the fiducial marker array as depicted in each of the initial and secondary surface scans.

4. The method of claim 2, wherein detecting the deviation comprises identifying a set of anatomical features in the patient depictions of each of the initial and secondary surface scans.

5. The method of claim 4, wherein detecting the deviation further comprises, determining a depicted position of the fiducial marker array relative to the set of anatomical features for each of the initial and secondary surface scans.

6. The method of claim 5, wherein detecting the deviation further comprises determining the deviation by comparing the depicted positions from the initial and secondary surface scans.

7. The method of claim 1, wherein receiving the initial surface scan and the secondary surface scan comprises receiving point cloud data from a handheld optical scanner.

8. The method of claim 1, further comprising receiving the intermediate surface scan as point cloud data from an optical scanner mounted to the medical imaging device.

9. The method of claim 8, wherein registering the intermediate surface scan to the tracking system frame of reference comprises:
retrieving a preconfigured position of the optical scanner relative to the medical imaging device from a memory; and
registering the point cloud data to the tracking system frame of reference based on the position of the medical imaging device and the preconfigured position of the optical scanner.

10. A computing device for maintaining patient registration, the computing device comprising a processor coupled with a communications interface, the communications interface coupled with an optical scanner and a medical imaging device, and the processor configured to:
obtain a position of a patient in a tracking system frame of reference based on a fiducial marker array affixed in a first position relative to the patient;
receive an initial surface scan of the patient and the fiducial marker array in the first position from the optical scanner,
receive an intermediate surface scan of the patient prior to receiving an intraoperative image from the medical imaging device;
determine a further position of the patient in the tracking system frame of reference based on a comparison of the intermediate surface scan and the initial surface scan by:
registering the intermediate surface scan to the tracking system frame of reference,
registering the initial surface scan to the intermediate surface scan,
determining a virtual position for the fiducial marker array based on the registration of the initial surface scan with the intermediate surface scan, and
determine the further position of the patient based on the virtual position;
obtain a position of the medical imaging device in the tracking system frame of reference; and
select an imaging configuration based on a comparison of the further position and the position of the medical imaging device.

11. The computing device of claim 10, wherein the processor is further configured to:
control the medical imaging device to capture the intraoperative image according to the imaging configuration; and
responsive to capturing, the intraoperative image of the patient by the medical imaging device:
obtain a position, in the tracking system frame of reference, of the fiducial marker array affixed in a second position relative to the patient;
receive a secondary surface scan depicting the patient and the fiducial marker array in the second position;
detect a deviation in a position of the fiducial marker array relative to the patient between the initial and secondary surface scans; and
apply the deviation to the further position of the patient to generate an updated position of the patient in the tracking system frame of reference, based on the fiducial marker array affixed in the second position.

12. The computing device of claim 11, wherein the processor is further configured to detect the deviation by:
registering the initial and secondary surface scans to a common frame of reference based on the patient as depicted in each of the initial and secondary surface scans;
determining the deviation by comparing the positions of the fiducial marker array as depicted in each of the initial and secondary surface scans.

13. The computing device of claim 11, wherein the processor is further configured to detect the deviation by identifying a set of anatomical features in the patient depictions of each of the preliminary and secondary surface scans.

14. The computing device of claim 13, wherein the processor is further configured to detect the deviation by determining a depicted position of the fiducial marker array relative to the set of anatomical features for each of the initial and secondary surface scans.

15. The computing device of claim 14, wherein the processor is further configured to detect the deviation by determining the deviation by comparing the depicted positions from the initial and secondary surface scans.

16. The computing device of claim 10, wherein the processor is further configured to receive the initial surface scan and the secondary surface scan as point cloud data from the optical scanner.

17. The computing device of claim 10, wherein the processor is further configured to receive the intermediate surface scan as point cloud data from the optical scanner.

18. The computing device of claim 17, wherein the processor is further configured to register the intermediate surface scan to the tracking system frame of reference by:
retrieving a preconfigured position of the optical scanner relative to the medical imaging device from a memory; and
registering the point cloud data to the tracking system frame of reference based on the position of the medical imaging device and the preconfigured position of the optical scanner.

19. A non-transitory computer-readable medium storing a plurality of instructions executable by a computing device comprising a processor for maintaining patient registration, the plurality of instructions configuring the processor to:
- obtain a position of a patient in a tracking system frame of reference based on a fiducial marker array affixed in a first position relative to the patient;
- receive an initial surface scan from the surface scanner of the patient and the fiducial marker array in the first position;
- receive an intermediate surface scan of the patient prior to receiving an intraoperative image from a medical imaging device;
- determine a further position of the patient in the tracking system frame of reference based on a comparison of the intermediate surface scan and the initial surface scan by:
    - registering the intermediate surface scan to the tracking system frame of reference,
    - registering the initial surface scan to the intermediate surface scan,
    - determining a virtual position for the fiducial marker array based on the registration of the initial surface scan with the intermediate surface scan, and
    - determining the further position of the patient based on the virtual position;
- obtain a position of the medical imaging device in the tracking system frame of reference; and
- select an imaging configuration based on a comparison of the further position and the position of the medical imaging device.

20. The medium of claim 19, wherein the processor is further configured to:
- control the medical imaging device to capture the intraoperative image according to the imaging configuration; and
- responsive to capturing the intraoperative image of the patient by the medical imaging device:
    - obtain a position, in the tracking system frame of reference, of the fiducial marker array affixed in a second position relative to the patient;
    - receive a secondary surface scan depicting the patient and the fiducial marker array in the second position;
    - detect a deviation in a position of the fiducial marker array relative to the patient between the initial and secondary surface scans; and
    - apply the deviation to the further position of the patient to generate an updated position of the patient in the tracking system frame of reference, based on the fiducial marker array affixed in the second position.

* * * * *